US00PP22930P2

(12) United States Plant Patent
Usami

(10) Patent No.: US PP22,930 P2
(45) Date of Patent: Aug. 7, 2012

(54) ***BEGONIA* PLANT NAMED 'USAMI N'**

(50) Latin Name: *Begonia×hiemalis*
Varietal Denomination: Usami N

(75) Inventor: Tatsuo Usami, Aichi (JP)

(73) Assignee: Suntory Flowers Ltd., Tokyo (JP)

( * ) Notice: Subject to any disclaimer, the term of this patent is extended or adjusted under 35 U.S.C. 154(b) by 0 days.

(21) Appl. No.: 13/385,064

(22) Filed: Jan. 31, 2012

(51) Int. Cl.
*A01H 5/00* (2006.01)

(52) U.S. Cl. ..... Plt./344

(58) Field of Classification Search ..... Plt./344
See application file for complete search history.

*Primary Examiner* — Annette Para
(74) *Attorney, Agent, or Firm* — C. A. Whealy

(57) ABSTRACT

A new and distinct cultivar of *Begonia* plant named 'Usami N', characterized by its upright and mounded plant habit; freely branching habit; leaves with finely-serrated margins; large and showy frilled double flowers with numerous tepals that are pale yellow and various shades of pink in color and held above and beyond the foliar plane; and excellent post-production longevity.

1 Drawing Sheet

Botanical designation: *Begonia×hiemalis.*
Cultivar denomination: 'USAMI N'.

BACKGROUND OF THE INVENTION

The present invention relates to a new and distinct cultivar of *Begonia* plant, botanically known as *Begonia×hiemalis*, commercially known as Elatior *Begonia* and hereinafter referred to by the name 'Usami N'.

The new *Begonia* plant is a naturally-occurring branch mutation of *Begonia×hiemalis* 'Renaissance Maria', not patented. The new *Begonia* was discovered and selected by the Inventor on a single flowering plant within a population of plants of 'Renaissance Maria' in a controlled greenhouse environment in Aichi, Japan in April, 2009.

Asexual reproduction of the new *Begonia* plant by vegetative cuttings taken in a controlled greenhouse environment in Aichi, Japan since April, 2009 has shown that the unique features of this new *Begonia* plant are stable and reproduced true to type in successive generations.

SUMMARY OF THE INVENTION

Plants of the new *Begonia* have not been observed under all possible environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of 'Usami N'. These characteristics in combination distinguish 'Usami N' as a new and distinct *Begonia* plant:

1. Upright and mounded plant habit.
2. Freely branching habit.
3. Leaves with finely-serrated margins.
4. Large and showy frilled double flowers with numerous tepals that are pale yellow and various shades of pink in color and held above and beyond the foliar plane.
5. Excellent postproduction longevity.

Plants of the new *Begonia* differ primarily from plants of the parent, 'Renaissance Maria', in flower color as plants of 'Renaissance Maria' have dark pink-colored flowers.

Plants of the new *Begonia* can be compared to plants of *Begonia×hiemalis* 'Renaissance Eden', disclosed in U.S. Plant Pat. No. 21,950. In side-by-side comparisons conducted in Aichi, Japan, plants of the new *Begonia* differed primarily from plants of 'Renaissance Eden' in the following characteristics:

1. Plants of the new *Begonia* had shorter lateral branches than plants of 'Renaissance Eden'.
2. Plants of the new *Begonia* had slightly smaller leaves than plants of 'Renaissance Eden'.
3. Plants of the new *Begonia* had smaller flowers than plants of 'Renaissance Eden'.
4. Plants of the new *Begonia* and 'Renaissance Eden' differed in flower color as plants of 'Renaissance Eden' had yellow and orange-colored flowers.
5. Plants of the new *Begonia* had shorter peduncles and pedicels than plants of 'Renaissance Eden'.

BRIEF DESCRIPTION OF THE PHOTOGRAPHS

The accompanying colored photographs illustrate the overall appearance of the new *Begonia* plant showing the colors as true as it is reasonably possible to obtain in colored reproductions of this type. Colors in the photographs may differ slightly from the color values cited in the detailed botanical description which accurately describe the colors of the new *Begonia* plant.

The photograph at the top of the sheet comprises a side perspective view of a typical flowering plant of 'Usami N' grown in a container.

The photograph at the bottom of the sheet is a close up view of a typical flowering plant of 'Usami N'.

DETAILED BOTANICAL DESCRIPTION

The aforementioned photographs and following observations and measurements describe plants grown during the winter in Aichi, Japan, under commercial practices in 15-cm containers in a polyethylene-covered greenhouse. During the production of the plants, the day temperatures ranged from 10° C. to 35° C. and the night temperatures ranged from 15° C. to 25° C. Plants were eight months old when the photographs and description were taken. In the following description, color references are made to The Royal Horticultural Society Colour Chart, 2001 Edition, except where general terms of ordinary dictionary significance are used.

Botanical classification: *Begonia×hiemalis* 'Usami N'.

Parentage: Naturally-occurring branch mutation of *Begonia× hiemalis* 'Renaissance Maria', not patented.

Propagation:

*Type*.—By terminal vegetative cuttings.

*Time to develop roots, summer*.—About 25 days at temperatures of 26° C. to 35° C.

*Time to develop roots, winter*.—About 30 days at temperatures of 16° C. to 20° C.

*Time to produce a rooted young plant, summer*.—About 40 days at temperatures of 26° C. to 35° C.

*Time to produce a rooted young plant, winter*.—About 45 days at temperatures of 16° C. to 20° C.

*Root description*.—Fine, fibrous; white in color.

*Rooting habit*.—Freely branching; plants of the new *Begonia* have not been observed to form tubers.

Plant description:

*Plant form and growth habit*.—Upright and mounded plant habit, broad inverted triangle; freely branching with good stem strength; flowers are fully double and positioned above the foliar plane; moderately vigorous growth habit; vegetative shoots are formed at basal nodes and flowering shoots are formed at upper nodes.

*Plant height*.—About 21.5 cm.

*Plant width*.—About 35.5 cm.

*Lateral branches*.—Length: About 7.8 cm. Diameter: About 1.1 cm. Internode length: About 1.4 cm. Aspect: Upright to outwardly. Texture: Sparsely pubescent. Color: Close to 146A.

*Leaves*.—Arrangement: Alternate; simple. Fully expanded leaves, length: About 11.5 cm. Fully expanded leaves, width: About 9.8 cm. Shape: Roughly reniform, asymmetrical. Apex: Acute. Base: Cordate; asymmetric. Margin: Finely double-serrate. Texture, upper and lower surfaces: Smooth, glabrous. Venation pattern: Palmate. Color: Developing leaves, upper surface: Close to 137A. Developing leaves, lower surface: Close to 148B. Fully expanded leaves, upper surface: Close to N137A; venation, close to 146C. Fully expanded leaves, lower surface: Close to 137D; venation, close to 146C. Petioles: Length: About 3.2 cm. Diameter: About 8.2 mm. Texture, upper and lower surfaces: Sparsely pubescent. Color, upper and lower surfaces: Close to 144A.

Flower description:

*Flowering habit*.—Large frilled double flowers with tepals arranged in axillary cymes; usually two to four flowers per cyme and about 13 cymes developing per plant; flowers positioned above and beyond the foliar plane; flowers face upright to outwardly.

*Natural flowering season*.—Plants begin flowering about 90 days after planting; plants will flower year round regardless of nyctoperiod, however plants flower earlier, more abundantly and continuously from the beginning of September until the end of June in Japan; flowers not persistent.

*Fragrance*.—None detected.

*Flowers*.—Shape: Rounded; rose-like. Diameter: About 4.7 cm. Depth (height): About 5.4 cm.

*Flower buds*.—Length: About 1.4 cm. Diameter: About 1.2 cm. Shape: Globose. Color: Close to 150D.

*Tepals*.—Arrangement: Rosette. Quantity per flower: Numerous, typically about 40 to 160 per flower. Size: Outer tepals, length: About 3 cm. Outer tepals, width: About 3.4 cm. Inner tepals, length: About 7 mm to 33 mm. Inner tepals, width: About 7 mm to 34 mm. Shape: Rounded to obovate. Apex: Rounded to obtuse. Base: Rounded to obtuse. Margin: Crenate, frilled; undulate. Texture, upper and lower surfaces: Smooth, glabrous. Color, outer tepals: When opening, upper surface: Close to 54B. When opening, lower surface: Close to 50C. Fully opened, upper surface: Close to 43D. Fully opened, lower surface: Close to 49B. Color, inner tepals: When opening, upper surface: Close to 2D and 55D. When opening, lower surface: Close to 2D and 56C. Fully opened, upper surface: Close to 2D and 48D. Fully opened, lower surface: Close to 2D and 49C.

*Flower bracts*.—Length: About 29.8 mm. Width: About 25.1 mm. Color: Close to N34B to N34C.

*Peduncles*.—Angle: Outwardly. Length: About 4.7 cm. Diameter: About 3.5 mm. Texture: Pubescent. Color: Close to 144A.

*Pedicels*.—Angle: Outwardly. Length: About 2.8 cm. Diameter: About 2.4 mm. Texture: Smooth, glabrous. Color: Close to 144A.

*Reproductive organs*.—Stamens: None observed. Pistils: None observed. Seeds and fruits: Seed and fruit production have not been observed on plants of the new *Begonia* as reproductive organs are not formed.

Postproduction longevity: Excellent postproduction longevity, plants of the new *Begonia* last about five months.

Disease/pest resistance: Resistance to pathogens and pests common to *Begonia* plants has not been observed.

Temperature tolerance: Plants of the new *Begonia* have been observed to tolerate temperatures from about 15° C. to about 35° C.

It is claimed:

1. A new and distinct *Begonia* plant named 'Usami N' as illustrated and described.

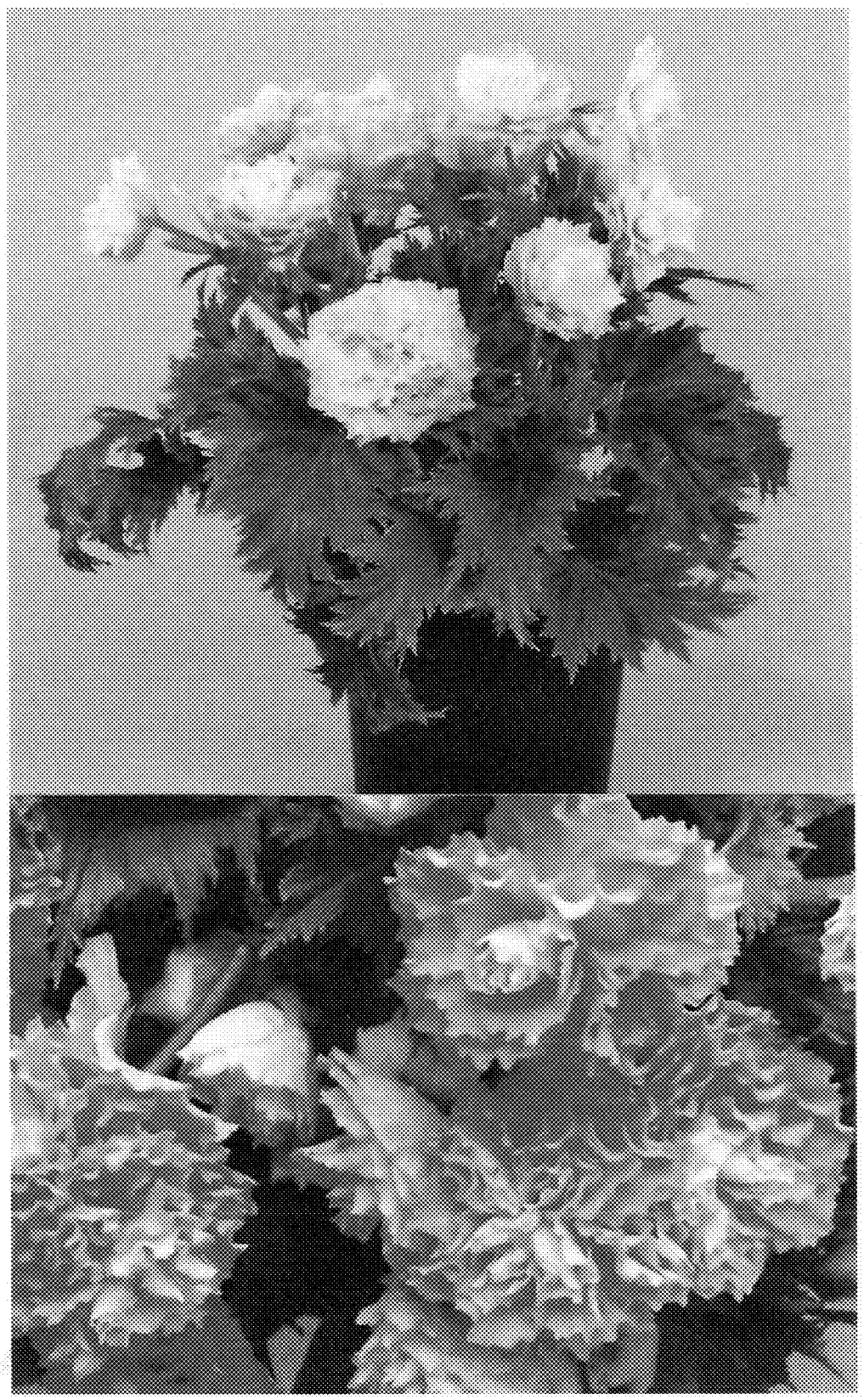

* * * * *